United States Patent [19]
Read et al.

[11] Patent Number: 5,843,696
[45] Date of Patent: Dec. 1, 1998

[54] BIOASSAY FOR TOXIC SUBSTANCES ACTIVATED BY METABOLIC ENZYME SYSTEM

[75] Inventors: Harry W. Read; Karl Gustavson; George A. Blondin, all of Madison, Wis.

[73] Assignee: Wisconsin Alumni Research Foundation, Madison, Wis.

[21] Appl. No.: 551,384

[22] Filed: Nov. 1, 1995

[51] Int. Cl.$^6$ .................................................. C12Q 1/26
[52] U.S. Cl. .............................................. 435/25; 435/975
[58] Field of Search .................. 435/4, 7, 7.21, 435/25, 288, 975, 7.2

[56] References Cited

U.S. PATENT DOCUMENTS

| | | | |
|---|---|---|---|
| 4,769,321 | 9/1988 | Self | 435/7 |
| 4,808,517 | 2/1989 | Blondin et al. | 435/4 |
| 5,149,656 | 9/1992 | Bitton et al. | 435/288 |
| 5,198,336 | 3/1993 | Knobeloch | 435/4 |
| 5,413,915 | 5/1995 | Case et al. | 435/25 |
| 5,420,011 | 5/1995 | Manger et al. | 435/7.21 |
| 5,478,723 | 12/1995 | Parkinson et al. | 435/4 |

OTHER PUBLICATIONS

Rydström, J., et al., "Factors Governing the Kinetics and Steady State of the Mitochondrial Nicotinamide Nucleotide Transhydrogenase System," *Eur. J. Biochem.*, 17: 56–62 (1970).

Sazanov, L.A., and J. B. Jackson, "Activation and Inhibition of Mitochondrial Transhydrogenase by Metal Ions," *Biochim. Biophys. Acta*, 1144: 225–228 (1993).

Anderson et al, "Purification and Partial Characterization of Bovine Heart Mitochondrial Pyridine Dinucleotide Transhydrogenase," *Archives of Biochemistry and Biophysics* 187:180–190 (1978).

*Primary Examiner*—John Knight
*Assistant Examiner*—Dameron Jones
*Attorney, Agent, or Firm*—Quarles & Brady

[57] ABSTRACT

A method for bioassaying for metabolic activation of toxicants from a xenobiotic compound by a metabolic enzyme system includes incubating the xenobiotic compound with a metabolic enzyme system known to produce toxicants during normal metabolic degradation processes and with a mitochondrial membrane preparation competent for enzymatic electron transfer. The production of a toxicant has a detrimental effect upon the electron transfer activity of the mitochondrial membrane preparation which can readily be assayed by observing changes in concentration of a selected redox indicator.

43 Claims, 4 Drawing Sheets

BIOASSAY FOR TOXIC SUBSTANCES ACTIVATED BY METABOLIC ENZYME SYSTEM

FIELD OF THE INVENTION

The present invention relates generally to the field of chemical toxicity testing or toxic testing in the environment and relates, in particular, to a rapid and convenient toxicity screening procedure.

BACKGROUND OF THE INVENTION

In recent years it has been widely recognized that many commercial and industrial chemicals can, even in very low amounts, cause toxic effects on humans, domesticated animals, and fish and wildlife. Such toxicants can be present in trace amounts in pharmaceuticals, food additives, industrial and agricultural products and can produce acute or chronic adverse somatic effects in humans or animals exposed to or ingesting these materials, as well as mutagenic, teratogenic or carcinogenic effects. It has therefore become commonplace in modern society to test the newly synthesized chemical or products for an array of toxic effects. However, many of these effects are difficult to assess even though they may cause illness in humans or animals exposed to such substances. It also becomes increasingly important to be able to test processed materials or substances of unknown constituency, or food products for the presence of contaminants of a toxic character.

It is therefore quite useful to have assays which can identify toxic substances or detect them in samples of material of unknown consistency. Ideally such assays would be qualitative as well as quantitative indicating the type of chemical substance which is detected if a positive result is obtained from the assay. However the qualitative chemical analysis of an unknown sample of toxic substances is at present a very slow and expensive technological effort. Mixtures of various toxic substances can present special difficulties because of the need to conduct separate analyses for the constituents thereof. The situation can be further complicated when multiple toxic substances are present in a single sample since the interaction between the toxicants can result in additive, synergistic, or antagonistic interactions thus making the results extremely difficult to predict. Nevertheless, even if qualitative analysis (identification of a particular toxicant) is impractical, sensitive quantitative analysis of samples to be screened for the presence of deleterious, even if unknown, toxicants is of great use in determining the safety of substances in the human or animal environment.

One generalized approach to the problem of sensitive testing for the presence of adverse toxic chemicals in a sample is to use biological materials which are extremely sensitive in the assays. These bioassays typically measure the response of a biological preparation or whole organism to challenges from the test chemical or environmental sample of unknown constituents to see if the preparation or organism is affected. Such a bioassay will not identify the chemicals concerned but will quantitatively measure their effect on biological activity. It has been found that data from certain bioassay tests correlate well with the effect on laboratory animals and humans when determined by conventional toxicological or epidemiological methods. Various prior assays have been based on simple enzymes or groups of enzyme tests or on the responses of whole organisms such as bacteria or fish which are exposed to the samples in question. One commercial system utilizes the light output of a bioluminescent bacterium to determine the biological response of the bacterium to toxicological effects of the test chemical or environmental sample being tested.

It has previously been reported that a bioassay for toxic substances is practical based on the use of submitochondrial particles. This bioassay using submitochondrial particles, known as the reverse electron transport, or RET assay has been used with another test referred to as the electron transport, ETr, to accurately predict the aquatic and cellular toxicity of a variety of chemicals. The assay is based on the use of submitochondrial particles having an intact mitochondrial membrane containing competent enzymes therein and the use of appropriate antibiotics to block the flow of electrons so that reactions can be selectively driven so as to favor reactions the product of which can be determined spectrophotometrically. A suitable reaction which may be catalyzed using the RET process is a conversion of $NAD^+$ to NADH. The presence of toxic substances in the test sample which interfere with the functioning of competent mitochondrial enzymes or the competency of the mitochondrial lipid membrane itself would disrupt the functioning of the RET electron flow system, the disruption of which can be detected by the change in photometric response of the solution. The RET bioassay is described in U.S. Pat. No. 4,808,517.

Prooxidants constitute another category of toxic substances which are capable of exerting toxicity on living organisms. U.S. Pat. No. 5,198,336 describes an assay employing submitochondrial membrane preparations to assay for the presence of toxic substances that induce prooxidant states. The assay depends upon the facilitated withdrawal of electrons from mitochondrial enzyme complex III toward a toxicant. The induction of prooxidants is quantified by spectrophotometric analysis of a reduced redox indicator.

Another source of compounds that exhibit toxic effects on humans and animals are the biological metabolic enzyme systems designed to detoxify harmful compounds. Many of the initial steps in the detoxification and excretion of chemicals foreign to living organisms (i.e., xenobiotics) are carried out by enzymes present in liver and other tissues. In many cases, however, the transformation of a xenobiotic by these enzymes can yield one or more products that are more toxic than the parent xenobiotic compound. These products are often unstable and highly reactive, and cause damage to cell components that can result in tissue necrosis, organ dysfunction, mutations, cancer or death.

The most important xenobiotic-transforming enzymes are the metabolic enzymes of the cytochrome P-450 system. Cytochrome P-450 enzymes metabolize a broad range of chemical compounds, and while each type of enzyme possesses a unique array of metabolic capabilities, the enzymes are considered to be isoenzymes because significant overlap exists in their activities. Although cytochrome P-450 enzymes are found in many different tissues, not every isoenzyme is necessarily present in each tissue. The most abundant and diverse arrays of cytochrome P-450 enzymes are generally found in the liver.

Because existing SMP-based toxicity tests lack cytochrome P-450 enzymes, the toxicity tests have limited predictive value for detecting toxicants generated during xenobiotic detoxification by the cytochrome P-450 or other metabolic enzyme system.

Other short-term bioassays have been devised that incorporate toxicant activation by liver microsomes, the most well-known being the Salmonella mutagenicity or the Ames test (Maron and Ames, 1983) and the Mutatox™ Photobacterium test (Ulitzur et al., 1980). While these assays are quite sensitive, they serve to assess the potential of toxicant metabolites to cause mutations in DNA, not damage to mitochondria or other cell constituents.

SUMMARY OF THE INVENTION

The present invention is summarized in that a method for assaying for the presence of toxicants generated during detoxification by a metabolic P-450 enzyme system comprises the steps of preparing a suspension of mitochondrial membranes containing competent electron transport enzyme complexes, adding to the suspension a metabolic enzyme system for detoxifying xenobiotics, adding a quantity of a test sample, and subsequently measuring a conversion of a redox indicator caused by the presence in the test sample of a compound metabolically activated to become a toxicant.

It is an object of the present invention to provide a method for detecting and identifying toxic substances that arise during nominal detoxification by the metabolic enzymes.

It is another object of the present invention to provide a kit for use in performing a bioassay to detect and identify such toxic chemicals. Such a kit includes suitable substrates and materials so that the assays for such toxic chemicals can be quickly and easily performed.

Other objects, advantages, and features of the present invention will become apparent from the following specification, taken in conjunction with the accompanying drawings.

DESCRIPTION OF THE PREFERRED EMBODIMENT

The method and kit using the bioassay of the present invention make use of mitochondrial preparations as biological assay tools intended to identify or detect the presence of a specific class of toxicants in a sample of unknown constituency. Such mitochondrial preparations have been described before and represent an attractive compromise between the over-simplification of most in vitro assays and the time-consuming and expensive nature of sophisticated assays conducted with whole organisms. The test described here has high sensitivity and is selective to a specific class of toxic chemicals acting through a common modality of toxicity.

Mitochondria are cellular organelles which are often characterized as being the biochemical power plant of eukaryotic cells since mitochondria have the basic biochemical enzymes required to oxidize nutrients at the cellular level to produce energy for the cell. In addition, mitochondria have enzymes performing a variety of other metabolic and ion transfer functions within the cell which require a highly organized system of enzymes in membrane structures. The enzymes of critical interest are those in the electron transport cascade which are carried on the inner membrane of mitochondria. The electron transport chain involves the flow of electrons to create energy storing and utilizing molecules within the cell.

Figure 1:
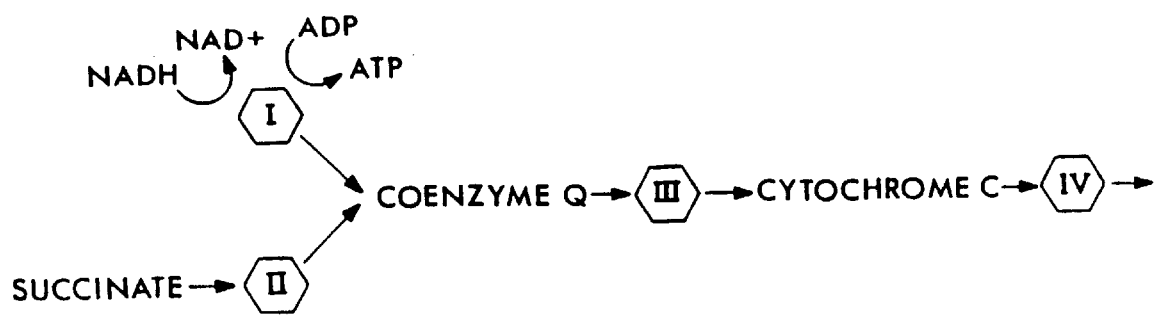
FIG. 1 shows electron transfer pathways of mitochondrial electron transfer enzyme complexes.

To better understand the method of action of the electron transport phenomenon utilized in the preferred embodiments of the present invention, it is necessary to consider the five different enzyme complexes conventionally recognized in the oxidative phosphorylation chain in mitochondria. As can be viewed in FIG. 1, enzyme complex I catalyzes the reduction of NADH to $NAD^+$ at the same time that ADP is converted to ATP in reaction. Electron flow is from the enzyme complex I toward coenzyme Q and from thereafter to enzyme complex III. Meanwhile, succinate is oxidized in enzyme complex II to produce an alternative source of electron flow into the system. From coenzyme Q, the electron flow proceeds through enzyme complex III to cytochrome c to enzyme complex IV, which ultimately transfers electrons to molecular oxygen. Each of the enzyme complexes in the oxidative phosphorylation chain can be inhibited selectively by individual toxicants. For example, complex I can be inhibited by rotenone, complex II by thenoyltrifluoroacetone, complex III by antimycin, complex IV by cyanide, and complex V by oligomycin. It is particularly the inhibitory effect of antimycin on enzyme complex III which is of use in the practice of one embodiment of the present invention. Each of the enzyme complexes consists of a series of enzymes embedded in the inner mitochondrial membrane and linked together for efficient interaction. Thus, in addition to being subject to specific inhibition, each complex depends on the competency of the membrane for successful operation. The membrane contains other enzymes, such as ATPase.

Figure 2:
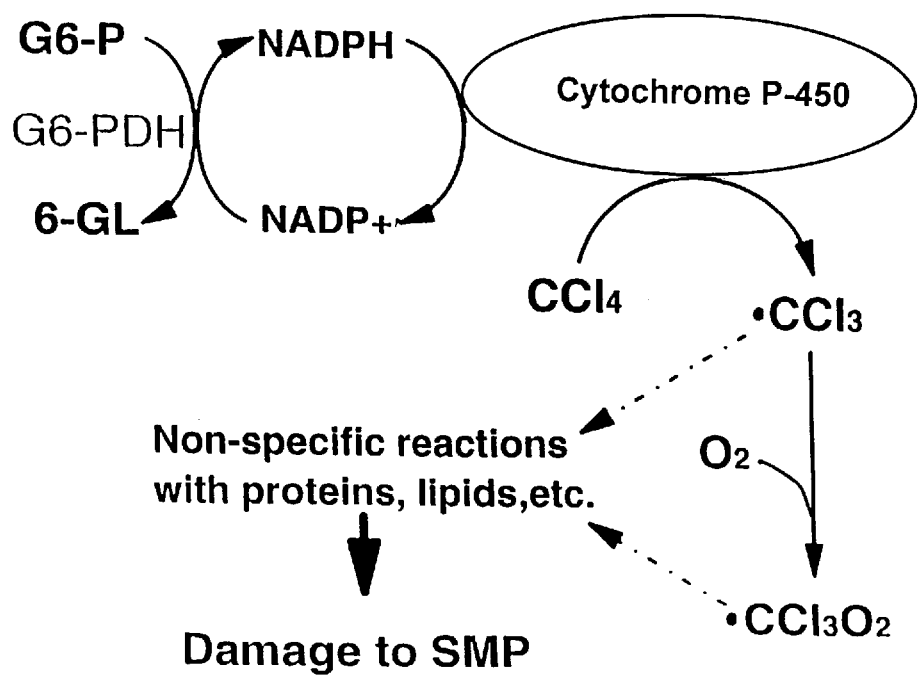
FIG. 2 shows the chemistry of cytochrome P-450 oxidation, and the inhibiting effect of toxic compounds activated by cytochrome P-450 enzymes on submitochondrial particles.

For a certain class of chemicals, i.e., those which are generated in the course of nominal detoxification of xenobiotics by metabolic enzyme systems such as the NADPH-dependent cytochrome P-450 enzyme system, the mechanism by which the toxic chemicals are formed includes the oxidation of the xenobiotic and the formation therefrom of a reactive oxygen radical, as is shown in FIG. 2. These radicals react non-specifically with proteins, lipids, and other cellular components in vivo or act as uncouplers of the exchange of energy between mitochondrial membrane constituents, thereby interfering with normal cell processes. It is for this reason that the presence of at least portions of the mitochondrial electron transport enzyme cascade are useful in an in vitro assay to detect the presence of such radical compounds generated by the cytochrome P-450 enzyme system or other such systems. These same interfering effects observed in vivo can be observed in preparations comprising mitochondrial membranes, the enzymatic activity of which is altered in the presence of such compounds.

The present invention is directed toward the creation of a bioassay and a mitochondrial test preparation kit to test for the presence of toxicants induced by a metabolic enzyme system, preferably the cytochrome P-450 enzymes. Therefore, to practice this invention, it is appropriate to have a mitochondrial preparation that includes a competent mitochondrial inner membrane carrying thereon the appropriate enzymes or enzyme complexes. The competent enzyme complexes that must be present in a particular mitochondrial membrane preparation will vary depending upon the test to be performed. Although the assays described herein have different enzyme requirements, it has been found that submitochondrial particles (SMP) prepared according to a known method have desirable membrane integrity and include the necessary enzyme complexes, coenzymes, and cofactors to support either test. Where necessary, the activity of a particular component is readily eliminated, as is described elsewhere herein. Thus, submitochondrial particles are the preferred mitochondrial membrane preparation.

The source of the submitochondrial particles used is not critical. Conventional mitochondrial preparations such as rabbit heart, rat liver, rat kidney, rat brown fat, or unfractionated beef heart mitochondria, may be used, and whole or partial preparations of any such mitochondria are usable within the present process. The preferred mitochondrial preparation for use in the present invention is, however, submitochondrial particles. Submitochondrial particles are bilayer lipid vesicals resulting from micelle formation from the fragments of cristae membranes when whole mitochondria are ruptured. In essence, whole mitochondria from any of the above sources are ruptured by sonication or detergents such as digitonin or treatment in a French press, separated from cytosolic residues by centrifugation, and the membrane segments are then allowed to reform into vesicles which model the behavior of the intact inner membrane of mitochondria. Such submitochondrial particles have the asset, in addition to modeling mitochondrial behavior, that they may be prepared and frozen or freeze-dried for storage and quantity, so that aliquots of the submitochondrial preparation can be readily available for use in conducting toxicant assays over a long period of time.

The preparation of submitochondrial particles for use in the practice of the present invention therefore begins with the preparation of whole mitochondria. Whole mitochondria from any available source can be used by any known technique capable of reliably separating mitochondria. Beef-heart mitochondria are relatively easy to prepare by the method described by Crane, et al. in Biochem. Biophys. Acta 22:475–487 (1956) or by the method described by Blondin and Green in Arch. Biochem. Biophys. 132:509–523 (1969). The heavy fraction of mitochondria isolated by the procedure described by Hatefi and Lester in Biochem. Biophys. Acta 27:83–85 (1958) gives a more standard preparation which has longer viability. The submitochondrial particles themselves can be prepared from either fresh or frozen mitochondria preferably by the method described by Hanson and Smith in Biochem. Biophys. Acta 81:214–222 (1964). Such submitochondrial particles once prepared can be stored or shipped frozen at −20° C. in a preserving mixture such as that described by Lenaz and MacLennan in J. Biol. Chem. 241:5260–5265 (1966). Alternatively, for storage and shipment the submitochondrial particles can be freeze-dried via the procedure described by Jolly, et al. in Arch. Biochem. Biophys. 130:191–211 (1969). The frozen preparations prepared by this process can simply be thawed to be ready for use in the practice of the present invention. The freeze-dried preparations can be simply reconstituted by wetting with the assay medium shortly before use. It is also possible, in theory, to provide purified enzyme complexes, co-enzymes, and co-factors in a biologically active form for use in the present bioassay.

In the method of the present invention, the mitochondrial membrane preparations thus described are mixed with a xenobiotic compound of a test sample, and with a metabolic enzyme system competent to transform xenobiotic compounds into at least one metabolically-activated toxicant. The mixture is then incubated under conditions of concentration, time, and temperature adequate to accomplish the transformation. The conditions will vary depending upon the choice of metabolic enzyme system, and one of ordinary skill in the art can determine the most suitable conditions for any given system. It has been determined that it is preferred that the reactants present in the incubation step be provided at high concentration to enhance the production of metabolic toxicants. As noted above, the conditions required to generate toxicants are independent of the test conditions used subsequently to determine whether one or more toxicants have, in fact, been generated.

Functional cytochrome P-450 is found in homogenates of livers taken from freshly-killed animals, including rats, mice or rabbits. Extensive research on the nature of cytochrome P-450 enzymes has been carried out using centrifugally isolated fractions of liver homogenates known as S-9, which can be stored frozen and reconstituted with little loss of activity. S-9 contains microsomes, fragments of cellular endoplasmic reticulum, which are membranous structures in which cytochrome P-450 enzymes are embedded.

A competent cytochrome P-450 metabolic enzyme system, which is the preferred metabolic enzyme system, is readily provided in the form of a liver microsome preparation, preferably made from livers of male or female rats that have previously been treated with an inducer of the cytochrome P-450 system. Exposure to certain chemical inducers stimulates production of the cytochrome P-450 enzymes, although the pattern of stimulation differs for each chemical inducer and not every isoenzyme is stimulated to the same degree. Inducers typically enhance production of the P-450 isoenzymes that will metabolize compounds having structures similar to the inducer. Such inducers are well known, and it is understood that the choice of inducer largely determines the spectrum of metabolic activity induced. Two such chemical inducers are phenobarbital and β-naphthoflavone.

Therefore, it is important to select a suitable inducer if one desires to detect metabolic toxicants of a particular class. Likewise, if a more wide-ranging analysis of toxicants is desired, it would be desirable to perform the assay of the present invention using liver microsomes preparations derived from a number of different inductions. It is anticipated that, although there may be some cross-reactivity between induced preparations, the ability of a liver microsome preparation to direct metabolic activation of xenobiotic compounds in this assay will largely depend upon the inducer used, as is the case in vivo.

Liver microsomes can be prepared using known methods, such as that of Van der Hoeven, T. A. and M. J. Coon, "Preparation and Properties of Partially Purified Cytochrome P-450 and Reduced Nicotinamide Adenine Dinucleotide Phosphate-Cytochrome P-450 Reductase from Rabid Liver Microsomes," *J. Biol. Chem.*, 249:6302–6310 (1974).

Cytochrome P-450 enzymes require NADPH as a reducing co-enzyme to function as expected. Therefore, when cytochrome P-450 is the selected metabolic enzyme system, it is desirable to provide a regenerating source of NADPH. This is readily provided by including in the assay vessel an enzymatic system that generates NADPH. A preferred system includes glucose 6-phosphate dehydrogenase enzyme, glucose 6-phosphate, and $NADP^+$ in suitable quantity to ensure the continued production of NADPH.

When the present assay includes submitochondrial particles, rat liver microsomes induced for cytochrome P-450 activity, and a source of NADPH in addition to the test compound, the mixture can be incubated at 37° C. for 15–60 minutes, preferably 15–45 minutes, most preferably 20 minutes, which conditions are sufficient to generate an adequate amount of metabolic toxicants for subsequent detection.

Although the P-450 enzymes are the preferred enzymatic system because they are well characterized and readily provided in a convenient form for the bioassay, other systems that produce toxicants from otherwise non-toxic compounds can also be used in the present method. To substitute another enzymatic system, one would simply need to determine suitable in vitro conditions (time, temperature, pH, and the like) under which the enzyme system could function to, for example, produce radicals from a xenobiotic compound. Subsequent redox assays could be performed exactly as described herein.

After the metabolic enzyme system has had an adequate opportunity to act upon the test compound, the effect of a toxic metabolite upon mitochondrial electron transport enzyme activity can readily be monitored. It is necessary to calibrate the system that measures the responsiveness of the submitochondrial particles to insult by the toxicant. Accordingly, it is necessary to measure the production or depletion of an enzyme product or substrate over a period of time to determine the effect on the enzyme cascade caused by the metabolic product of the environmental sample to which the particles are exposed. Although it is possible to measure respiration rate directly, such measurements at present require sophisticated instrumentation and technique.

It is preferred for the purposes of the present invention that submitochondrial particles be used and that the response of the enzyme systems residing the particles be measured in as simple a way as possible. One very simple and direct way is to monitor changes in the concentration of NADH spectrophotometrically at 340 nm. This natural coenzyme undergoes the following reversible redox reaction:

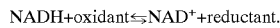

The reduced form (NADH) absorbs light strongly at 340 nm while the oxidized form absorbs light only very weakly at 340 nm, making monitoring optical absorbance at 340 nm using a spectrophotometer a very simple and useful means of determining rates of reactions involving this coenzyme. It is noted, however, that NADPH, required for cytochrome P-450 function, also absorbs at 340 nm, interfering with the determination of NADH. To avoid this problem in assays that use the cytochrome P-450 enzymes to metabolize toxicants, it is necessary to (1) ensure that NADPH is maintained in a reduced state by means of a regenerating system; and (2) dilute the product of the incubation step sufficiently to reduce the absorbance at 340 nm by NADPH to an acceptable low background level over which the change in NADH concentration can be determined. At the same time, this dilution step reduces the opacity of the mixture that would otherwise preclude spectrophotometric analysis.

The goal of monitoring changes in concentration of a redox indicator can be accomplished using either an electron transfer (ETr) test, which measures the ability of mitochondrial electron transfer enzyme complexes to oxidize a redox indicator such as NADH, or using a reverse electron transfer (RET) assay described in U.S. Pat. No. 4,808,517, incorporated herein by reference, where the ATP-driven reduction of a redox indicator, such as the reduction of $NAD^+$ to NADH, is monitored. Other redox indicators known to the art could also be used are monitored in the present invention. These include thionicotinamide and adenine dinucleotide. However, NADH and its counterpart $NAD^+$ are preferred because they are the natural components of the enzyme system and, as such, are likely optimal agents in the system.

Figure 3:
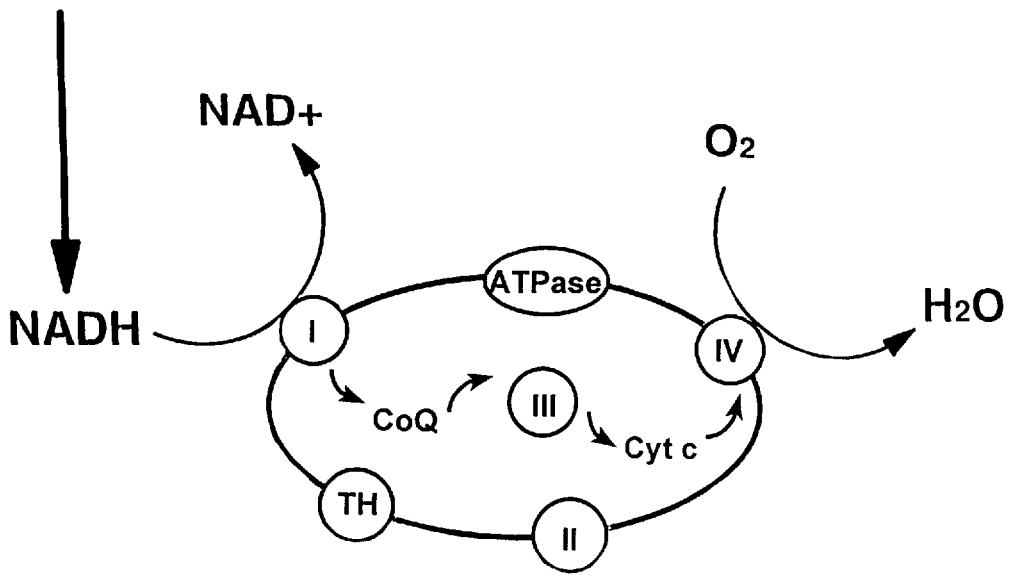
FIG. 3 shows the electron transfer pathway of mitochondrial electron transfer enzyme complexes in an electron transfer test.

The electron transfer assay portion of the present invention is simple and straightforward. As shown in FIG. 3, competent enzyme complexes I, III, and IV in the mitochondrial membrane preparation are able to oxidize NADH to $NAD^+$. Thus, upon addition of NADH, under suitable reaction conditions, to the test vessel, a net decrease in NADH concentration is expected. Any disruption or uncoupling of the mitochondrial enzymes of complexes I, III, and IV results in a reduced ability to oxidize NADH and, therefore, a slower decrease in NADH concentration than would have been expected. The rate of change in NADH concentration is readily monitored spectrophotometrically at 340 nm.

Figure 4:
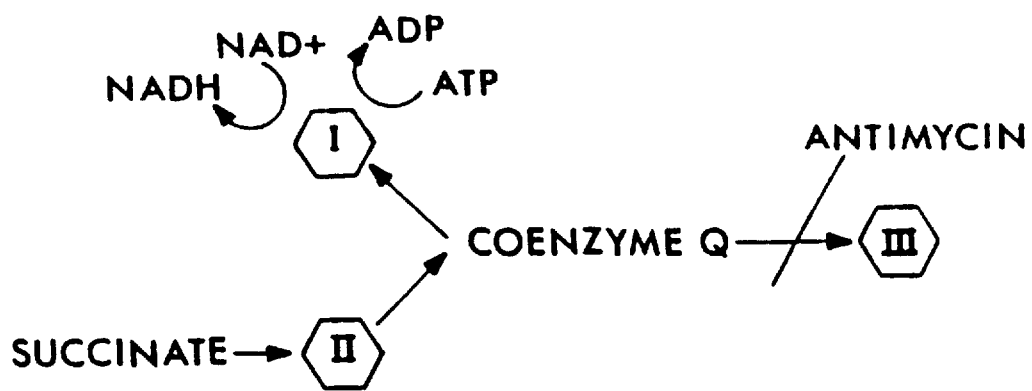
FIG. 4 shows the electron transfer pathway of mitochondrial electron transfer enzyme complexes in a reverse electron transfer test.

In substance, the reverse electron transfer assay portion of the present invention, shown in FIG. 4, reverses the electron transfer which would normally occur from the enzyme complex I to coenzyme Q. This occurs by inhibiting the function of enzyme complex III by antimycin, and then making an excess of succinate for complex II enzymes. The effect of this is to drive an endergonic reduction of $NAD^+$ to NADH as long as there is sufficient presence of ATP. For the process to be effective, therefore, there must be a sufficient quantity of $NAD^+$ in the sample preparation to serve as a substrate for conversion by competent enzymes. It may also be required that other enzymes such as glutamate, or alcohol or pyruvate dehydrogenases be added from exogenous sources in the event these materials are lost by rupture of the intact mitochondria during particle preparation.

As can be seen, if the enzymes and membranes of the mitochondrial preparations are competent, succinate will be consumed while $NAD^+$ will be reduced to NADH as long as sufficient ATP is present. The process can be monitored spectrophotometrically to quantify the production of NADH.

An assay medium is also necessary to perform the bioassay using either the electron transfer test or the reverse electron transfer test. The assay medium should contain suitable buffers, and should contain the necessary substrates and inhibitors appropriate to drive the desired enzyme effect.

When the assay is the electron transfer test, the assay medium should contain suitable buffers and sugars, such as a Tris-chloride buffer and sucrose, and should also contain the substrates and inhibitors necessary to drive the mitochondrial enzymes to or from a reaction product which can be measured. A magnesium salt may be appropriate to avoid sensitivity to calcium in the sample by the system.

For a reverse electron transport assay in which $NAD^+$ is to be reduced to NADH, one obvious requirement of the assay medium is $NAD^+$ to be a substrate. To supply a source of electrons, succinate is a preferred substrate which can be oxidized by the complex II enzymes. In order to couple the donor electrons from succinate conversion to $NAD^+$ reduction, it is necessary to block transport of the electron flow through complex III enzymes. This can be easily accomplished by adding antimycin, a known inhibitor of the complex III enzymes. With this combination, if the mitochondrial membranes and enzymes are otherwise functional, electrons would flow from coenzyme Q back through complex I enzymes to $NAD^+$. Thus $NAD^+$ would be reduced to NADH, as long as ATP was present to energize the conversion. Thus, the initiation of the reaction can be controlled by the timing of ATP addition. While these particular substrates, inhibitor and energy source are preferred, other combinations are possible. For example, it is possible to derive energy for the reaction from coupling in the cytochrome oxidase complex by oxidation of ascorbate via the intermediate tetra-p-phenylenediamine in place of coupling in the ATPase complex with ATP. By varying the election and combinations of buffers, substrates, energizers and enzyme inhibitors in the assay medium, the sensitivity of the test toward certain toxicants or types of toxicants (e.g. inhibitors of enzyme complex IV such as cyanide) can be greatly increased. Such variations in the assay medium offers the possibility of discriminating among different types of toxicants during analysis of environmental samples.

It is noted that the reagents used in the described RET test are similar to those used in conventional RET tests, but higher levels of magnesium and an increased pH were used to effectively inhibit the activity of mitochondrial transhydrogenase which would otherwise have catalyzed reduction of $NAD^+$ from NADPH, independent of the normal reverse electron transfer reaction. Another method for inhibiting mitochondrial transhydrogenase function would include the use of monoclonal antibody to block the active site of the enzyme.

One advantage of these monitoring assays is that the reactants can be simply admixed in a common receptacle, since the reaction can be controlled by withholding a reaction component until desired. Normally, for convenience, the ETr or RET assay is run at 25° C., but any temperature between about 10° C. and 45° C. is suitable. As long as the reaction product, such as NADH, is to be assayed spectrophotometrically, the assay can most conveniently be performed in a spectrophotometer cuvette. Most cuvettes, such as the conventional 1 cm path length quartz cuvette, are usable in the present invention although it has been found that using a cuvette with 5 cm path length enables a lowering of protein concentration and an increase in sensitivity to many toxicants by as much as a factor of five times.

Preferably the RET assay may be conducted by adding the assay medium and the redox indicator directly to the cuvette in which the metabolic reaction has taken place. A baseline reading of optical adsorbency can then be taken. The system can then be energized, as by addition of ATP, and adsorbency to remeasured after a standard time period, such as two minutes. To obtain a standard calibration curve and derive an effective response of 50%, successive tests at differing concentrations of toxicants (or xenobiotic compound) must be performed so that dose-response can be calculated based on inhibition as plotted against the log of toxicant (or xenobiotic) concentration. Longer preincubation times, i.e. for 10 minutes, before adding the ATP or other energizing agent increases the sensitivity to some toxicants, as does increasing the reaction temperature.

To measure unknown concentrations of known or suspected toxicants in test samples, absorbance measured with the test sample is compared with the appropriate calibration curve. In the case of known toxicants this absorbance reading gives a quantitative analysis of the toxicant concentration in the sample. In the case of unknown toxicants, the shape of the dose-response curve obtained with various volumes of sample or separate chemical analysis can reveal the nature of the toxicant or toxicants of concern. However, the assay will generally be used simply to screen for general toxicity as a prelude to closer chemical or toxicological investigation by other qualitative methods. The assay can thus be efficiently used as a screening test to avoid repetitive testing on those samples which are free from toxicants so that monitoring programs can achieve savings and concentrate further testing on the samples of valid concern.

In general calibration curves can be used to determine the presence or absence of toxicants in water from a wide variety of suspect sources, e.g. industrial plant or municipal sewage treatment plant effluents, seepage from sanitary or secure landfills, or groundwater near pesticide storage and mixing areas. In areas known to be contaminated, to an unknown degree by a known toxicant, the calibration curves for that toxicant can be used to determine toxicant levels in all waste or wash streams associated with the toxicant. More generally, the method of the present invention can be used to show involvement of a metabolic enzyme system in the generation of toxicants, to assess the quality of water samples as part of a larger battery of tests, and as an aid in characterizing and identifying toxicants and other compounds which, while not themselves toxic, can be made toxic by the detoxification systems of human and other animal species.

The present invention is more fully understood by reference to the following non-limiting examples.

EXAMPLES

The practice of the present invention began with the creation of submitochondrial particles prepared from beef heart mitochondria according to the method of Hansen, M. and A. L. Smith, "Studies on the Mechanism of Oxidative Phosphorylation. VII. Preparation of a Submitochondrial Particle (ETPH) Which is Capable of Fully Coupled Oxidative Phosphorylation," *Biochem. Biophys. Acta,* 81:214–222 (1964). The submitochondrial particles were frozen in aliquots and thawed as needed. Liver microsomes (S-9 preparations) were taken from rats that had previously been treated with a P-450-inducing chemical. The S9 preparations were then further purified by centrifugation at 105, 000×g. The supernatant was discarded and the pellet containing the purified liver microsomes was resuspended. This procedure effectively removed soluble enzymes that would otherwise have interfered in the assays. The SMP prepared as described were adjusted to 24 mg/ml protein, frozen and stored at –80° C.

Livers were taken from male fisher 344 rats that had been injected with a solution of phenobarbital inducer or β-naphthoflavone, as noted below, (60 milligrams/kilogram body weight) on each of three days prior to sacrifice. The livers were processed according to Van der Hoeven, T. A. and M. J. Coon, "Preparation and Properties of Partially Purified Cytochrome P-450 and Reduced Nicotinamide Adenine Dinucleotide Phosphate-Cytochrome P-450 Reductase from Rabid Liver Microsomes," *J. Biol. Chem.,* 249:6302–6310 (1974). This processing produced suspensions of purified microsomes (39 mg/ml protein) that were frozen and stored at –80° C. until used.

The bioassays were conducted in optical cuvettes, in two stages. First, the SMP, the liver microsomes, and a system for continuously regenerating NADPH were incubated in a cuvette with a test compound. NADPH drives the cytochrome P-450-mediated reaction by acting as a reducing coenzyme. To maintain NADPH levels, glucose 6-phosphate dehydrogenase enzyme glucose 6-phosphate and $NADP^+$ were included.

Specifically, 300 microliters of a 0.1M potassium phosphate solution (pH 7.5) was added to a 1-centimeter spectrophotometric glass cuvette. Ten microliters of a test compound dissolved in a solvent were added. When the test compound was carbon tetrachloride, the solvent was ethanol. When the test compound was anthracene, the solvent was dimethylsulfoxide (DMSO). Control samples received pure solvent containing no test compound. One hundred Al of glucose 6-phosphate (42.6 mM) and glucose 6-phosphate dehydrogenase (EC 1.1.1.49, 7.5 units/ml) were then added.

The SMP were diluted with cold phosphate buffer (pH 7.5) to a concentration of 1 mg/ml. The SMP suspension (100 µl) and the liver microsomes (10 µl) at 39 mg/ml protein were added. When the test compound was carbon tetrachloride, the liver microsomes were obtained from rats treated with phenobarbital. When the test compound was anthracene, the liver microsomes were obtained from rats treated with β-naphthoflavone. Secondary controls received bovine serum albumin (39 mg/ml) instead of microsomes.

Finally, 50 µl of NADP$^+$ (10 mM) was added and the cuvettes were immediately placed in a 37° C. water bath for 45 minutes. This incubation procedure was followed without regard to whether the detecting assay was the ETr test or the RET test. After the incubation, however, the subsequent steps differed.

ETr Assay

An ETr test was performed to measure the effect on mitochondrial enzyme activity of metabolically-activated toxicants of carbon tetrachloride. In samples analyzed according to the ETr test, the cuvettes were then removed from the water bath and 2.4 ml of 0.1M, 25° C. phosphate buffer (pH 7.5) was added. The cuvettes were maintained at ambient temperature for the remainder of the assay. Optical absorbance at 340 nm was measured twice with a four minute interval to establish a base line. The ETr reaction was then initiated by adding 50 µl of NADH (8.2 mM), and absorbance was measured 15 seconds later and again after 5 minutes. When compared with the control that lacked a test compound, NADH oxidase activity was inhibited by an average of 51% at the highest concentration of carbon tetrachloride, as measured by a decrease in absorbance at 340 nm. The secondary control which included the carbon tetrachloride test compound but lacked liver microsomes, showed 4% inhibition at all tested concentrations. Using a conventional ETr protocol, not linked to the cytochrome P-450 detoxification enzymes, carbon tetrachloride elicited no inhibition at the tested concentrations. This result indicates that carbon tetrachloride is only able to inhibit NADH oxidation by SMP after being activated by the cytochrome P-450 detoxifying enzymes. This further demonstrates the utility of the disclosed method for revealing toxicants generated in a metabolic pathway that would otherwise be undetected in prior assays.

RET assay

An RET test was performed to measure the effect on mitochondrial enzyme activity of metabolically-activated toxicants of anthracene. The incubated mixture was removed from the water bath and diluted using 2.35 ml of a buffer (25° C.) containing 50 mM EPPS (pH 8.0), 16.6 mM MgSO$_4$, 5 mM succinate, 1 mM NAD$^+$ and 0.2 µg/ml antimycin. The baseline optical absorbance was then measured at 340 nm before the RET reaction was initiated by adding 50 µl of 0.2M ATP with mixing. Five subsequent absorbance readings were taken at 6 minute intervals, and the rate of increase in optical absorbance was measured. At the highest concentration of anthracene (1 ppm), the rate of increase was 68% slower than a control containing DMSO only. Secondary controls, containing 1 ppm anthracene but lacking liver microsomes showed no inhibition.

In similar experiments using microsomes from phenobarbital-induced rats, bromobenzine and acetamidophenol at 69 and 42.5 ppm, respectively, elicited 68% and 89% inhibition relative to controls lacking the test compound, and elicited 22% inhibition in controls containing the test compound but lacking microsomes. This slower rate of increase was attributed either to damage to SMP or to the presence of another inhibitory substance.

The present invention is not intended to be limited to the foregoing examples, but to encompass all such modifications as come within the scope of the appended claims.

We claim:

1. A method for detecting a metabolically-activated toxicant of a xenobiotic compound in an environmental sample to be tested, the method comprising the steps of:
   (a) incubating a mixture comprising a mitochondrial membrane suspension comprising competent electron transport enzyme complexes thereon, the sample to be tested, a metabolic enzyme system competent to transform the xenobiotic compound into at least one metabolically-activated toxicant, and a first redox indicator required for activity of the metabolic enzyme system under conditions of concentration, time, and temperature adequate to accomplish the transformation;
   (b) adding an assay medium and a second redox indicator which can be converted by the mitochondrial electron transport enzyme complexes to another compound while maintaining the first redox indicator in a reduced state; and
   (c) assaying for conversion of the second redox indicator, wherein a rate of conversion different from that of a control sample lacking the metabolic enzyme system indicates the existence of a metabolically-activated toxicant of the xenobiotic compound.

2. A method as claimed in claim 1 wherein the mitochondrial membrane suspension comprises submitochondrial particles.

3. A method as claimed in claim 1 wherein the competent metabolic enzyme system comprises NADPH-dependent cytochrome P-450 detoxifying enzymes.

4. A method as claimed in claim 3 further comprising a regenerating source of NADPH.

5. A method as claimed in claim 4 wherein the regenerating source of the NADPH comprises NADP$^+$, glucose-6-phosphate, and glucose 6-phosphate dehydrogenase.

6. A method as claimed in claim 1 wherein the metabolic enzyme system is provided in the form of liver microsomes.

7. A method as claimed in claim 1 wherein the mitochondrial membrane suspension comprises competent electron transport enzyme complexes I and II, coenzyme Q, and ATPase, and wherein the method comprises the following steps:

adding to the incubated mixture a buffered assay medium comprising the second redox indicator, an inhibitor of mitochondrial electron transfer by mitochondrial enzyme complex III, a source of electron flow into enzyme complex II, and an inhibitor of mitochondrial transhydrogenase-driven reduction of the second redox indicator;

determining a baseline concentration of a reduced form of the added second redox indicator;

providing ATP to direct an energy-linked transfer of electrons from the source of electron flow to the second redox indicator; and measuring a change in concentration of the reduced form of the second redox indicator over time, wherein a rate of change slower than that of a control sample lacking the metabolic enzyme system indicates the existence of a metabolically-activated toxicant of the xenobiotic compound.

8. A method as claimed in claim 7 wherein the assay medium has a pH value of about 8.0.

9. A method as claimed in claim 7 wherein the second redox indicator is NAD$^+$ and the reduced form of the second redox indicator is NADH.

10. A method as claimed in claim 9 wherein the concentration of the NADH is measured by spectrophotometric absorbance at 340 nm and wherein the buffered assay medium is added to allow measurement of the NADH concentration without significant interference by NADPH.

11. A method as claimed in claim 7 wherein the inhibitor of mitochondrial electron transfer by mitochondrial enzyme complex III is antimycin.

12. A method as claimed in claim 7 wherein the source of electron flow into enzyme complex II is succinate.

13. A method as claimed in claim 7 wherein the inhibitor of mitochondrial transhydrogenase-driven reduction of the second redox indicator is cationic magnesium.

14. A method as claimed in claim 1 wherein the mitochondrial membrane suspension comprises competent electron transport enzyme complexes I, III and IV, coenzyme Q, and cytochrome c, and wherein the method comprises the following steps:
adding to the incubated mixture a buffered assay medium;
adding the second redox indicator;
determining a baseline concentration of the added second redox indicator; and
measuring a decrease in the concentration of the second redox indicator over time, wherein a rate of decrease slower than that of a control sample lacking the metabolic enzyme system indicates the existence of a metabolically-activated toxicant of the xenobiotic compound.

15. A method as claimed in claim 14 wherein the second redox indicator is NADH.

16. A method as claimed in claim 15 wherein the concentration of the NADH is measured by spectrophotometric absorbance at 340 nm and wherein the buffered assay medium is added to allow measurement of the NADH concentration without significant interference by NADPH.

17. A method for detecting a metabolically-activated toxicant of a xenobiotic compound in an environmental sample to be tested, the method comprising the steps of:
(a) incubating a mixture comprising submitochondrial particles comprising competent electron transport enzyme complexes I and II, coenzyme Q, and ATPase, the sample to be tested, NADPH-dependent cytochrome P-450 detoxifying enzymes, and a regenerating source of NADPH, under conditions of concentration, time, and temperature adequate to form at least one metabolically-activated toxicant from the xenobiotic compound;
(b) adding to the incubated mixture a buffered assay medium comprising NAD$^+$, an inhibitor of mitochondrial electron transfer by mitochondrial enzyme complex III, a source of electron flow into enzyme complex II, and an inhibitor of mitochondrial transhydrogenase-driven reduction of NAD$^+$ while maintaining NADPH in a reduced state;
(c) determining a baseline concentration of NADH;
providing ATP to direct an energy-linked transfer of electrons from the source of electron flow to the NAD$^+$ to form NADH; and
(d) measuring a change in concentration of the NADH over time, wherein a rate of change slower than that of a control sample lacking the metabolic enzyme system indicates the existence of a metabolically-activated toxicant of the xenobiotic compound.

18. A method as claimed in claim 17 wherein the assay medium has a pH value of about 8.0.

19. A method as claimed in claim 17 wherein the concentration of the NADH is measured by spectrophotometric absorbance at 340 nm and wherein the buffered assay medium is added to allow measurement of the NADH concentration without significant interference by NADPH.

20. A method as claimed in claim 17 wherein the inhibitor of mitochondrial electron transfer by mitochondrial enzyme complex III is antimycin.

21. A method as claimed in claim 17 wherein the source of electron flow into enzyme complex II is succinate.

22. A method as claimed in claim 17 wherein the inhibitor of mitochondrial transhydrogenase-driven reduction of the second redox indicator is cationic magnesium.

23. A method for detecting a metabolically-activated toxicant of a xenobiotic compound in an environmental sample to be tested, the method comprising the steps of:
(a) incubating a mixture comprising submitochondrial particles comprising competent electron transport enzyme complexes I, III and IV, coenzyme Q, and cytochrome c, the sample to be tested, NADPH-dependent cytochrome P-450 detoxifying enzymes, and a regenerating source of NADPH, under conditions of concentration, time, and temperature adequate to form at least one metabolically-activated toxicant from the xenobiotic compound;
adding to the incubated mixture a buffered assay medium;
adding NADH;
determining a baseline concentration of the NADH; and
measuring a decrease in the concentration of the NADH over time, wherein a rate of decrease slower than that of a control sample lacking the metabolic enzyme system indicates the existence of a metabolically-activated toxicant of the xenobiotic compound.

24. A method as claimed in claim 23 wherein the concentration of the NADH is measured by spectrophotometric absorbance at 340 nm and wherein the buffered assay medium is added to allow measurement of the NADH concentration without significant interference by NADPH.

25. A kit for use in spectrophotometrically assaying for the presence in an environmental sample of a xenobiotic compound capable being metabolically activated into at least one toxicant, the kit comprising:
a mitochondrial membrane suspension comprising competent electron transport enzyme complexes, a metabolic enzyme system competent to transform the xenobiotic compound into at least one metabolically-activated toxicant, and a first redox indicator required for activity of the metabolic enzyme system under conditions of concentration, time, and temperature adequate to accomplish the transformation;
a second redox indicator;
an inhibitor of mitochondrial electron transfer by mitochondrial enzyme complex III;
a source of electron flow into enzyme complex II; and
an inhibitor of mitochondrial transhydrogenase-driven reduction of the second redox indicator.

26. A kit as claimed in claim 25 wherein the mitochondrial membrane suspension comprises submitochondrial particles.

27. A kit as claimed in claim 25 wherein the competent metabolic enzyme system comprises NADPH-dependent cytochrome P-450 detoxifying enzymes.

28. A kit as claimed in claim 27 further comprising a regenerating source of NADPH.

29. A kit as claimed in claim 28 wherein the regenerating source of the NADPH comprises NADP$^+$, glucose-6-phosphate, and glucose 6-phosphate dehydrogenase.

30. A kit as claimed in claim 25 wherein the metabolic enzyme system is provided in the form of liver microsomes.

31. A kit as claimed in claim 25 further comprising a buffered assay medium having a pH value of about 8.0.

32. A kit as claimed in claim 25 wherein the second redox indicator is $NAD^+$.

33. A kit as claimed in claim 25 wherein the inhibitor of mitochondrial electron transfer by mitochondrial enzyme complex III is antimycin.

34. A kit as claimed in claim 25 wherein the source of electron flow into enzyme complex II is succinate.

35. A kit as claimed in claim 25 wherein the inhibitor of mitochondrial transhydrogenase-driven reduction of the second redox indicator is cationic magnesium.

36. A kit for use in spectrophotometrically assaying for the presence in an environmental sample of a xenobiotic compound capable being metabolically activated into at least one toxicant, the kit comprising:

a mitochondrial membrane suspension comprising competent electron transport enzyme complexes, a metabolic enzyme system competent to transform the xenobiotic compound into at least one metabolically-activated toxicant, and a first redox indicator required for activity of the metabolic enzyme system under conditions of concentration, time, and temperature adequate to accomplish the transformation; and a second redox indicator.

37. A kit as claimed in claim 36 wherein the mitochondrial membrane suspension comprises submitochondrial particles.

38. A kit as claimed in claim 36 wherein the competent metabolic enzyme system comprises NADPH-dependent cytochrome P-450 detoxifying enzymes.

39. A kit as claimed in claim 38 further comprising a regenerating source of NADPH.

40. A kit as claimed in claim 39 wherein the regenerating source of the NADPH comprises $NADP^+$, glucose-6-phosphate, and glucose 6-phosphate dehydrogenase.

41. A kit as claimed in claim 36 wherein the metabolic enzyme system is provided in the form of liver microsomes.

42. A kit as claimed in claim 36 further comprising a buffered assay medium having a pH value of about 7.5.

43. A kit as claimed in claim 36 wherein the second redox indicator is NADH.

* * * * *